(12) United States Patent
Lee et al.

(10) Patent No.: US 9,834,768 B2
(45) Date of Patent: Dec. 5, 2017

(54) EFFECTIVE METHOD FOR SPECIFIC GENE SILENCING USING ARTIFICIAL SMALL RNA

(71) Applicant: KOREA ADVANCED INSTITUTE OF SCIENCE AND TECHNOLOGY, Daejeon (KR)

(72) Inventors: Younghoon Lee, Daejeon (KR); Geunu Bak, Daejeon (KR); Hongmarn Park, Daejeon (KR); Jee Soo Choi, Daejeon (KR); Won Kyeong Kim, Daejeon (KR); Shinae Suk, Daejeon (KR); Ji Young Lee, Daejeon (KR); Yeongseong Yoon, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 58 days.

(21) Appl. No.: 14/855,612

(22) Filed: Sep. 16, 2015

(65) Prior Publication Data
US 2016/0186169 A1    Jun. 30, 2016

(30) Foreign Application Priority Data

Dec. 31, 2014  (KR) .................. 10-2014-0196025
Jan. 7, 2015   (KR) .................. 10-2015-0002221

(51) Int. Cl.
  *C07H 21/02*   (2006.01)
  *G01N 33/554*  (2006.01)
  *C12N 15/113*  (2010.01)

(52) U.S. Cl.
  CPC ........ *C12N 15/113* (2013.01); *C12N 2310/11* (2013.01); *C12N 2310/531* (2013.01); *C12N 2330/51* (2013.01)

(58) Field of Classification Search
  None
  See application file for complete search history.

(56) References Cited

FOREIGN PATENT DOCUMENTS

| KR | 10-2005-0026384 | 3/2005 |
|---|---|---|
| KR | 10-2005-0057290 | 6/2005 |
| KR | 10-2007-0085457 | 8/2007 |
| KR | 10-2007-0091199 | 9/2007 |
| KR | 10-2013-0082474 | 7/2013 |

OTHER PUBLICATIONS

Hongmarn Park, et al., "Effects of different target sites on antisense RNA-mediated regulation of Gene expression", BMB Reports Nov. 2014; 47(11): 619-624, published online on Jan. 7, 2014 http://submit.bmbreports.org/Search/View.html?tr_num=2588&start=0&keyword.
Park, H., Bak, G., Kim, S. C. and Lee, Y., "Exploring sRNA-mediated gene silencing mechanisms using artificial small RNAs derived from a natural RNA scaffold in *Escherichia coli*", First Published online; Feb. 7, 2013, Nucleic Acids Res. 41, 3787-3804.
Kenneth J. Livak and Thomas D. Schmittgen, "Analysis of Relative Gene Expression Data Using Real-Time Quantitative PCR and the 2-[Delta][Delta]CT Method", Methods, 25(4):402-408, Dec. 2001.
Shuai Man et al., "Artificial trans-encoded small non-coding RNAs specifically silence the selected gene expression in bacteria", Nucleic Acids Research, Feb. 3, 2011, pp. 1-16.
Kook Han et al., "Recognition and discrimination of target mRNAs by Sib RNAs, a cis-encoded sRNA family", Nucleic Acids Research, 2010, vol. 38, No. 17, pp. 5851-5866, Published online May 7, 2010.

*Primary Examiner* — Jennifer Graser
(74) *Attorney, Agent, or Firm* — Lex IP Meister, PLLC (57) ABSTRACT

A nucleic acid molecule comprising a stem-loop structure, a nucleic acid complex comprising the nucleic acid molecule, a composition for delivering a target recognition sequence, and the composition comprising the nucleic acid complex. An artificial small ribonucleic acid of the stem-loop structure stably maintains single-strandedness of a target recognition sequence which interacts with a nucleic acid of interest for a gene of interest of a prokaryote, thereby providing a nucleic acid complex for effective silencing of the gene of interest.

15 Claims, 4 Drawing Sheets

FIG. 4

SEQUENCE LISTING

<160> NUMBER OF SEQ ID NOS: 23

<210> SEQ ID NO 1
<211> LENGTH: 23
<212> TYPE: RNA
<213> ORGANISM: Artificial Sequence
<220> FEATURE:
<223> OTHER INFORMATION: Synthetic (P1 stem-1)
<220> FEATURE:
<221> NAME/KEY: stem_loop
<222> LOCATION: (11)
<223> OTHER INFORMATION: n is loop region in stem_loop, and comprises 4
      or more RNA, wherein each RNA is independently selected from A, U,
      C, G, and modified RNAs thereof

<400> SEQUENCE: 1
gaagcugacc nggucaguuu ccc                                           23

<210> SEQ ID NO 2
<211> LENGTH: 27
<212> TYPE: RNA
<213> ORGANISM: Artificial Sequence
<220> FEATURE:
<223> OTHER INFORMATION: Synthetic (P1 stem-2)

<400> SEQUENCE: 2
gaagcugacc agaucgguca guuuccc                                       27

<210> SEQ ID NO 3
<211> LENGTH: 26
<212> TYPE: RNA
<213> ORGANISM: Artificial Sequence
<220> FEATURE:
<223> OTHER INFORMATION: Synthetic (P1 stem-3)

<400> SEQUENCE: 3
gaagcugacc aggaggucag uuuccc                                        26

<210> SEQ ID NO 4
<211> LENGTH: 28
<212> TYPE: RNA
<213> ORGANISM: Artificial Sequence -continued

```
<220> FEATURE:
<223> OTHER INFORMATION: Synthetic (Termination stem)

<400> SEQUENCE: 4
gggcccucgc uucggugagg gcuuuacc                                        28

<210> SEQ ID NO 5
<211> LENGTH: 20
<212> TYPE: RNA
<213> ORGANISM: Escherichia coli

<400> SEQUENCE: 5
uauuuuucau guaaagguaa                                                 20

<210> SEQ ID NO 6
<211> LENGTH: 20
<212> TYPE: RNA
<213> ORGANISM: Escherichia coli

<400> SEQUENCE: 6
uucauguaaa gguaauuuug                                                 20

<210> SEQ ID NO 7
<211> LENGTH: 20
<212> TYPE: RNA
<213> ORGANISM: Escherichia coli

<400> SEQUENCE: 7
guaaagguaa uuuugauguc                                                 20

<210> SEQ ID NO 8
<211> LENGTH: 20
<212> TYPE: RNA
<213> ORGANISM: Escherichia coli

<400> SEQUENCE: 8
aaaaaaacca ugaggguaau                                                 20

<210> SEQ ID NO 9
<211> LENGTH: 20
<212> TYPE: RNA
<213> ORGANISM: Escherichia coli

<400> SEQUENCE: 9
aaccaugagg guaauaaaua                                                 20

<210> SEQ ID NO 10
<211> LENGTH: 20
<212> TYPE: RNA
<213> ORGANISM: Escherichia coli

<400> SEQUENCE: 10
ugaggguaau aaauaaugau                                                 20

<210> SEQ ID NO 11
<211> LENGTH: 20
<212> TYPE: RNA
<213> ORGANISM: Artificial Sequence
<220> FEATURE:
<223> OTHER INFORMATION: Synthetic (cspE-1)

<400> SEQUENCE: 11
uuaccuuuac augaaaaaua                                                 20
```

```
<210> SEQ ID NO 12
<211> LENGTH: 20
<212> TYPE: RNA
<213> ORGANISM: Artificial Sequence
<220> FEATURE:
<223> OTHER INFORMATION: Synthetic (cspE-2)

<400> SEQUENCE: 12
caaaauuacc uuuacaugaa                                                   20

<210> SEQ ID NO 13
<211> LENGTH: 20
<212> TYPE: RNA
<213> ORGANISM: Artificial Sequence
<220> FEATURE:
<223> OTHER INFORMATION: Synthetic (cspE-3)

<400> SEQUENCE: 13
gacaucaaaa uuaccuuuac                                                   20

<210> SEQ ID NO 14
<211> LENGTH: 20
<212> TYPE: RNA
<213> ORGANISM: Artificial Sequence
<220> FEATURE:
<223> OTHER INFORMATION: Synthetic (ompF-1)

<400> SEQUENCE: 14
auuacccuca ugguuuuuuu                                                   20

<210> SEQ ID NO 15
<211> LENGTH: 20
<212> TYPE: RNA
<213> ORGANISM: Artificial Sequence
<220> FEATURE:
<223> OTHER INFORMATION: Synthetic (ompF-2)

<400> SEQUENCE: 15
uauuuauuac ccucaugguu                                                   20

<210> SEQ ID NO 16
<211> LENGTH: 20
<212> TYPE: RNA
<213> ORGANISM: Artificial Sequence
<220> FEATURE:
<223> OTHER INFORMATION: Synthetic (ompF-3)

<400> SEQUENCE: 16
aucauuauuu auuacccuca                                                   20

<210> SEQ ID NO 17
<211> LENGTH: 20
<212> TYPE: DNA
<213> ORGANISM: Artificial Sequence
<220> FEATURE:
<223> OTHER INFORMATION: Synthetic (cspE_F)

<400> SEQUENCE: 17
gtccaaagga ttcggtttca                                                   20

<210> SEQ ID NO 18
<211> LENGTH: 20
<212> TYPE: DNA
<213> ORGANISM: Artificial Sequence
<220> FEATURE:
<223> OTHER INFORMATION: Synthetic (cspE_R)
```

```
<400> SEQUENCE: 18
cagagcgatt acgtttgcag                                                    20

<210> SEQ ID NO 19
<211> LENGTH: 20
<212> TYPE: DNA
<213> ORGANISM: Artificial Sequence
<220> FEATURE:
<223> OTHER INFORMATION: Synthetic (ompF_F)

<400> SEQUENCE: 19
aggctttggt atcgttggtg                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic (ompF_R)

<400> SEQUENCE: 20
tgcgcaacta acagaacgtc                                                    20

<210> SEQ ID NO 21
<211> LENGTH: 4268
<212> TYPE: DNA
<213> ORGANISM: Artificial Sequence
<220> FEATURE:
<223> OTHER INFORMATION: Synthetic (pHM4T-dSL-SmaI)

<400> SEQUENCE: 21
ttgacattgt gagcggataa caatataatg aattcgaagc tgaccagatc ggtcagtttc         60
ccgggccctc gcttcggtga gggctttacc aagcttttgg ctgttttggc ggatgagaga        120
agattttcag cctgatacag attaaatcag aacgcagaag cggtctgata aaacagaatt        180
tgcctggcgg cagtagcgcg gtggtcccac ctgaccccat gccgaactca gaagtgaaac        240
gccgtagcgc cgatggtagt gtggggtctc cccatgcgag agtagggaac tgccaggcat        300
caaataaaac gaaaggctca gtcgaaagac tgggcctttc gttttatctg ttgtttgtcg        360
gtgaacgctc tcctgagtag acaaatccg ccgggagcgg atttgaacgt tgcgaagcaa         420
cggcccggag ggtggcgggc aggacgcccg ccataaactg ccaggcatca aattaagcag        480
aaggccatcc tgacggatgg cctttttgcg tttctacaaa ctcttttgtt tattttttcta       540 aatacattca aatatgtatc cgctcatgag acaataaccc tgataaatgc ttcaataata       600
ttgaaaaagg aagagtatga gtattcaaca tttccgtgtc gcccttattc cctttttttgc      660 ggcattttgc cttcctgttt ttgctcaccc agaaacgctg gtgaaagtaa agatgctga        720 agatcagttg ggtgcacgag tgggttacat cgaactggat ctcaacagcg gtaagatcct        780 tgagagttttt cgccccgaag aacgttttcc aatgatgagc acttttaaag ttctgctatg      840
tggcgcggta ttatcccgtg ttgacgccgg gcaagagcaa ctcggtcgcc gcatacacta        900
ttctcagaat gacttggttg agtactcacc agtcacagaa aagcatctta cggatggcat       960
gacagtaaga gaattatgca gtgctgccat aaccatgagt gataacactg cggccaactt       1020
acttctgaca acgatcggag gaccgaagga gctaaccgct ttttttgcaca acatgggga      1080 tcatgtaact cgccttgatc gttgggaacc ggagctgaat gaagccatac caaacgacga      1140
gcgtgacacc acgatgctgt agcaatggca acaacgttgc gcaaactatt aactggcgaa     1200
```

```
ctacttactc tagcttcccg gcaacaatta atagactgga tggaggcgga taaagttgca    1260
ggaccacttc tgcgctcggc ccttccggct ggctggttta ttgctgataa atctggagcc    1320
ggtgagcgtg ggtctcgcgg tatcattgca gcactggggc cagatggtaa gccctcccgt    1380
atcgtagtta tctacacgac ggggagtcag gcaactatgg atgaacgaaa tagacagatc    1440
gctgagatag gtgcctcact gattaagcat tggtaactgt cagaccaagt ttactcatat    1500
atactttaga ttgatttaaa acttcatttt taatttaaaa ggatctaggt gaagatcctt    1560
tttgataatc tcatgaccaa aatcccttaa cgtgagtttt cgttccactg agcgtcagac    1620
cccgtagaaa agatcaaagg atcttcttga gatccttttt ttctgcgcgt aatctgctgc    1680
ttgcaaacaa aaaaaccacc gctaccagcg gtggtttgtt tgccggatca agagctacca    1740
actctttttc cgaaggtaac tggcttcagc agagcgcaga taccaaatac tgtccttcta    1800
gtgtagccgt agttaggcca ccacttcaag aactctgtag caccgcctac atacctcgct    1860
ctgctaatcc tgttaccagt ggctgctgcc agtggcgata agtcgtgtct taccgggttg    1920
gactcaagac gatagttacc ggataaggcg cagcggtcgg gctgaacggg gggttcgtgc    1980
acacagccca gcttggagcg aacgacctac accgaactga gatacctaca gcgtgagcat    2040
tgagaaagcg ccacgcttcc cgaagggaga aaggcggaca ggtatccggt aagcggcagg    2100
gtcggaacag gagagcgcac gagggagctt ccagggggaa acgcctggta tctttatagt    2160
cctgtcgggt ttcgccacct ctgacttgag cgtcgatttt tgtgatgctc gtcaggggggg    2220
cggagcctat ggaaaaacgc cagcaacgcg gccttttac ggttcctggc cttttgctgg    2280
ccttttgctc acatgttctt tcctgcgtta tcccctgatt ctgtggataa ccgtattacc    2340
gcctttgagt gagctgatac cgctcgccgc agccgaacga ccgagcgcag cgagtcagtg    2400
agcgaggaag cggaagagcg cctgatgcgg tattttctcc ttacgcatct gtgcggtatt    2460
tcacaccgca tatgaggaca ccatcgaatg gtgcaaaacc tttcgcggta tggcatgata    2520
gcgcccggaa gagagtcaat tcagggtggg tgaatggtga aaccagtaac gttatacgat    2580
gtcgcagagt atgccggtgt ctcttatcag accgtttccc gcgtggtgaa ccaggccagc    2640
cacgtttctg cgaaaacgcg ggaaaaagtg gaagcggcga tggcggagct gaattacatt    2700
cccaaccgcg tggcacaaca actggcgggc aaacagtcgt tgctgattgg cgttgccacc    2760
tccagtctgg ccctgcacgc gccgtcgcaa attgtcgcgg cgattaaatc tcgcgccgat    2820
caactgggtg ccagcgtggt ggtgtcgatg gtagaacgaa gcggcgtcga agcctgtaaa    2880
gcggcggtgc acaatcttct cgcgcaacgc gtcagtgggc tgatcattaa ctatccgctg    2940
gatgaccagg atgccattgc tgtggaagct gcctgcacta atgttccggc gttatttctt    3000
gatgtctctg accagacacc catcaacagt attattttct cccatgaaga cggtacgcga    3060
ctgggcgtgg agcatctggt cgcattgggt caccagcaaa tcgcgctgtt agcgggccca    3120
ttaagttctg tctcggcgcg tctgcgtctg gctggctggc ataaatatct cactcgcaat    3180
caaattcagc cgatagcgga acgggaaggc gactggagtg ccatgtccgg ttttcaacaa    3240
accatgcaaa tgctgaatga gggcatcgtt cccactgcga tgctggttgc caacgatcag    3300
atggcgctgg gcgcaatgcg cgccattacc gagtccgggc tgcgcgttgg tgcggatatc    3360
tcggtagtgg gatacgacga taccgaagac agctcatgtt atatcccgcc gttaaccacc    3420
atcaaacagg attttcgcct gctggggcaa accagcgtgg accgcttgct gcaactctct    3480
cagggccagg cggtgaaggg caatcagctg ttgcccgtct cactggtgaa aagaaaaacc    3540
accctggcgc ccaatacgca aaccgcctct ccccgcgcgt tggccgattc attaatgcag    3600
```

```
ctggcacgac aggtttcccg actggaaagc gggcagtgag cgcaacgcaa ttaatgtaag      3660
ttagctcact cattaggcac cccaggcttt acactttatg cttccggctc gtataatgtg      3720
tggaattgtg agcggataac aatttcacac aggaaacagc tatgaccatg attacggatt      3780
cactggccgt cgttctcgag ctgcttgagc cagtgagcga ttgctggcct agatgaatga      3840
ctgtccacga cagaacccgg cttatcggtc agtttcacct gatttacgta aaaacccgct      3900
tcggcgggtt tttgcttttg gaggggcaga aagatgaatg actgtccacg acgctatacc      3960
caaaagaaag cggcttatcg gtcagtttca cctggtttac gtaaaaaccc gcttcggcgg      4020
gtttttgctt ttggaggggc agaaagatga atgactgtcc acgacactat acccaaaaga      4080
aagcggctta tcggtcagtt tcacctgttt tacgtaaaaa cccgcttcgg cgggttttta      4140
cttttggagg ggcagaaaga tgaatgactg tccacgacac tatacccaaa agaaagcggc      4200
ttatcggtca gttttacctg atgtacgtaa taaaccgttc cgggatccat aaatatgagc      4260
ggataaca                                                               4268

<210> SEQ ID NO 22
<211> LENGTH: 61
<212> TYPE: DNA
<213> ORGANISM: Artificial Sequence
<220> FEATURE:
<223> OTHER INFORMATION: Synthetic (pHM4T-dSL-SmaI-oligo1)

<400> SEQUENCE: 22
aattcgaagc tgaccagatc ggtcagtttc ccgggccctc gcttcggtga gggctttacc      60
a                                                                      61

<210> SEQ ID NO 23
<211> LENGTH: 61
<212> TYPE: DNA
<213> ORGANISM: Artificial Sequence
<220> FEATURE:
<223> OTHER INFORMATION: Synthetic (pHM4T-dSL-SmaI-oligo2)

<400> SEQUENCE: 23
agcttggtaa agccctcacc gaagcgaggg cccgggaaac tgaccgatct ggtcagcttc      60
g                                                                      61
```

EFFECTIVE METHOD FOR SPECIFIC GENE SILENCING USING ARTIFICIAL SMALL RNA

CROSS-REFERENCE TO RELATED APPLICATIONS

This application claims the benefit of Korean Patent Applications No. 10-2014-0196025 filed on Dec. 31, 2014 and Korean Patent Applications No. 10-2015-0002221 filed on Jan. 7, 2015 in the Korean Intellectual Property Office, the disclosures of which are herein incorporated by reference in their entirety.

TECHNICAL FIELD

The present disclosure relates to a nucleic acid molecule comprising a stem-loop structure, a nucleic acid complex comprising the nucleic acid molecule, a method of delivering a target recognition sequence comprise: contacting the nucleic acid complex with a prokaryote, a vector comprising DNA encoding the nucleic acid complex, and a cell transformed with the vector.

BACKGROUND

Bacterial small noncoding RNAs (sRNAs) play diverse roles as gene expression regulators in a variety of physiological processes. Generally, bacterial sRNAs modulate translation activity and/or endogenous stability of their target mRNAs via RNA-RNA base pairing. In *Escherichia coli* (*E. coli*), about a hundred species of sRNAs have been experimentally identified, and nearly half of these sRNAs have been functionally analyzed.

The majority of identified sRNAs is encoded in trans at different chromosomal locations from target genes, and usually suppresses target gene expression by inhibiting translation or inducing mRNA degradation with the aid of an abundant RNA chaperone protein, Hfq. Other sRNAs are encoded in cis on strands opposite their target. Unlike trans-encoded sRNAs, cis-encoded sRNAs have extensive regions capable of perfect base-pairing, but the actual base-pairing regions appear limited to specific sequences. Additionally, their functions are generally independent of Hfq.

Several researchers have attempted to design strategies for silencing or knockdown of specific genes by mimicking the general functions of sRNAs. In eukaryotes, induction of specific gene silencing by short interfering RNAs (siRNAs) has been extensively used for elucidating gene function and developing therapeutic agents. Similarly, gene silencing in bacteria could be achieved using artificial sRNA (afsRNA) loaded with well-defined target recognition sequences. To design effective afsRNAs in *E. coli*, factors that affect interactions with target mRNA should be considered, including accessibility of target site, base-pairing energy, secondary structures of target mRNA and afsRNA, off-target effects of afsRNA, and reaction kinetics.

That is, knockdown or silencing of a specific gene expression can be very effectively used for elucidating gene function. To date, efficient silencing methods have been established in eukaryotic cells, but not in bacteria. Accordingly, there is a demand for a new strategy for knockdown or silencing of specific genes in bacteria by using afsRNAs.

SUMMARY OF THE INVENTION

In one aspect, the present invention provides a nucleic acid molecule comprising a stem-loop structure, wherein the nucleic acid molecule comprising, consisting essentially of, or consisting of a nucleotide sequence of SEQ ID NO: 1.

In another aspect, the present invention provides a nucleic acid complex comprising a first nucleic acid molecule comprising the nucleotide sequence of SEQ ID NO: 1, a second nucleic acid molecule comprising a nucleotide sequence of SEQ ID NO: 4, and a target recognition sequence comprising a nucleotide linked between the first and second nucleic acid molecules.

Still in another aspect, the present invention provides a method of delivering a target recognition sequence comprise: contacting the nucleic acid complex with a prokaryote.

Still in another aspect, the present invention provides a vector comprising the nucleic acid molecule or DNA encoding the nucleic acid complex.

Still in another aspect, the present invention provides a cell transformed with the vector.

DETAILED DESCRIPTION

Accordingly, the present inventors have designed a nucleic acid molecule which confers single-strandedness to target recognition sequences, and this nucleic acid molecule may be utilized as an RNA scaffold that allows very easy embedding of target recognition sequences and also confers stability and single-strandedness to various target recognition sequences in cells to effectively silence particular bacterial genes.

The definition of terms used in the detailed description of the invention is as below:

As used herein, the term "sRNA (small RNA)" refers to a short-length RNA, which is usually 200 or less nucleotides in length, is not translated into a protein and effectively inhibits the translation of a specific mRNA by complementary binding.

As used herein, the term "gene" is intended to have the broadest meaning, and the gene may encode a structural protein, a regulatory protein, or a functional RNA. Herein, the regulatory protein comprises a transcriptional factor, a heat shock protein or a protein involved in DNA/RNA replication, transcription and/or translation. In the present invention, a target gene whose expression is to be inhibited may be present as an extrachromosomal element.

As used herein, the term "ARdSL RNA (antisense RNA in double stem loop scaffold)" refers to an artificial small ribonucleic acid (artificial small RNA; afsRNA) that allows embedding of target recognition sequences between two stem-loop structures tethered to the 5'- and 3'-ends in an RNA scaffold.

As used herein, the term "stem-loop structure" refers to a structure comprising a double-stranded stem and an intervening loop by base-pairing through hydrogen bonding inside a single stranded RNA molecule called as a hairpin structure. Such the stem-loop structure is very stable in cells, compared to a single-stranded structure.

As used herein, the term "P1 stem" is a sequence derived from M1 RNA which is the catalytic subunit of RNase P, and the P1 stem is crucial for in vivo stability of M1 RNA, and P1 stem-disrupted mutation of M1 RNA has a characteristic of causing its rapid degradation in cells.

M1 RNA is a very stable sRNA expressed from E. coli gene rnpB, and it has a length of 377 nt and a half-life of 60 minutes or longer. A loop region of P1 stem of wild-type M1 RNA corresponds to +12~+362 positions of M1 RNA, and it can be modified with various sequences without loss of in vivo stability.

As used herein, the term "terminator stem" is a sequence derived from SibC RNA which is an E. coli sRNA, and it is characterized that transcription is terminated immediately after transcription of RNA comprising this stem and RNA comprising this terminator stem has in vivo stability.

As used herein, the term "encoding" may be used to comprise encoding an RNA molecule comprising a base sequence complementary to a base sequence of a DNA molecule.

Hereinafter, the present invention will be described in more detail.

In one aspect, the present invention provides a nucleic acid molecule. Wherein the nucleic acid molecule may be a stem-loop structure, and specifically, the nucleic acid molecule may be represented by the following SEQ ID NO: 1:

SEQ ID NO: 1
GAAGCUGACC n GGUCAGUUUCCC wherein the n is a loop structural RNA sequence consisting of 4 or more RNA bases, for example, an RNA sequence consisting of 4 to 438, 4 to 400, 4 to 100, 4 to 50, 4 to 10, 10 to 438, 10 to 400, 10 to 100, 10 to 50, 42 to 438, 42 to 400, 42 to 100, or 42 to 50 RNA bases, and the RNA bases are each independently selected from the group consisting of A, G, C, U, and modified bases thereof.

In an embodiment, the nucleic acid molecule of SEQ ID NO: 1 may consisting of a base sequence of SEQ ID NO: 2 or SEQ ID NO: 3.

As used herein, the "stem-loop structure", called as a hairpin structure, refers to a structure comprising a double-stranded RNA stem, which are formed by hydrogen bonding between inverted repeat sequences and an intervening RNA loop in a contiguous RNA. Specifically, the stem structure is formed by complementary binding of entire or partial sequences at the 5'- and 3'-ends relative to "n", and the "n" has a loop structure. Since the structure has this feature, specific type of the base is not limited as long as "n" forms the loop structure between the stem structures at the 5'- and 3'-ends. In another aspect, the present invention provides a nucleic acid complex consisting of a first nucleic acid molecule, a second nucleic acid molecule, and a target recognition sequence consisting of 10 to 40 nucleotides linked between the first and second nucleic acid molecules.

In an embodiment, the first nucleic acid molecule may have a nucleotide sequence consisting of total 26 to 460, 26 to 422, 26 to 222, 26 to 200, 26 to 122, 26 to 100, 26 to 72, 26 to 50, 64 to 460, 64 to 422, 64 to 222, 64 to 200, 64 to 122, 64 to 100, or 64 to 72 RNA bases comprising the nucleotide sequence of SEQ ID NO: 1, for example, the nucleotide sequence of SEQ ID NO: 2 or 3.

Further, the second nucleic acid molecule may consist a nucleotide sequence of SEQ ID NO: 4.

Further, the first nucleic acid molecule and/or the second nucleic acid molecule may have a stem-loop structure.

Further, the first nucleic acid molecule may be located at the 5'-end of the nucleic acid complex, which is linked to the 5'-end of the target recognition sequence. The second nucleic acid molecule may be located at the 3'-end of the nucleic acid complex, which is linked to the 3'-end of the target recognition sequence.

Specifically, the nucleic acid complex may comprise the first nucleic acid molecule comprising the nucleotide sequence of SEQ ID NO: 1, the target recognition sequence comprising total 10 to 40 nucleotides, which is linked to the 3'-end of the first nucleic acid molecule, and the second nucleic acid molecule comprising the nucleotide sequence of SEQ ID NO: 4, which is linked to the 3'-end of the target recognition sequence.

The list of the sequences of SEQ ID NO: 1 to SEQ ID NO: 4 are given in the following Table 1.

TABLE 1

| SEQ ID NO. | Name | Sequence (5' -> 3') |
|---|---|---|
| SEQ ID NO: 1 | P1 stem-1 | GAAGCUGACC n GGUCAGUUUCCC |
| SEQ ID NO: 2 | P1 stem-2 | GAAGCUGACCAGAUCGGUCAGUUUCCC |
| SEQ ID NO: 3 | P1 stem-3 | GAAGCUGACCAGGAGGUCAGUUUCCC |
| SEQ ID NO: 4 | Termination stem | GGGCCCUCGCUUCGGUGAGGGCUUUACC |

The nucleic acid complex may further comprise a nucleic acid linker which links the 3'-end of the first nucleic acid molecule and the 5'-end of the target recognition sequence, and the linker may have a nucleotide sequence of total 1 to 20, 1 to 15, 1 to 10, 4 to 20, 4 to 15, or 4 to 10.

The target recognition sequence may be one or more selected from the group consisting of RNA, RNA aptamer, antisense RNA, and ribozyme, which are hybridizable to a specific region of a nucleic acid (e.g., mRNA) of interest, and it may be a sequence consisting of total 10 to 40, 10 to 30, 15 to 25, or about 20 nucleotides. Further, the target recognition sequence may complementarily bind to one or more sequences of the nucleic acid of interest, and for example, 1 to 40, 1 to 30, 1 to 20, 1 to 10, 10 to 40, 10 to 30, 10 to 20, or about 20 consecutive nucleotide sequences of the nucleic acid of interest. Specifically, the target recognition sequence may form one or more complementary binding to the ribosome binding site (RBS) present in the nucleic acid of interest, and for example, it may form complementary binding to at least one binding nucleotide of the ribosome binding site (RBS) present in the nucleic acid of interest, or complementary binding to 10 to 20 consecutive nucleotide sequences comprising binding nucleotides in the nucleic acid of interest.

The "binding nucleotide" is a nucleotide that exists in the ribosome binding site of the nucleic acid of interest and forms complementary binding to the target recognition sequence.

The "aptamer" refers to an oligonucleotide binding to a specific target, and for example, an RNA aptamer.

The "antisense RNA" refers to RNA or a derivative thereof comprising a nucleotide sequence complementary to a specific mRNA sequence, and it has a characteristic of binding to the complementary sequence of mRNA to inhibit translation of mRNA into a protein. The antisense RNA sequence of the present invention refers to an RNA sequence which is complementary to mRNA of the target gene and is able to bind to mRNA of the gene of interest, and the antisense RNA sequence is able to inhibit translation of mRNA of the gene of interest, maturation, or any other activity essential to overall biological functions.

The "ribozyme" is one of RNAs and has an enzymatic function of recognizing a specific RNA sequence to catalyze the self-cleaving of RNA. The ribozyme is composed of a region capable of specifically binding to a complementary base sequence of the mRNA strand of the gene of interest and a region capable of cleaving mRNA of the gene of interest.

As used herein, the "target recognition sequence" refers to a sequence that forms complementary binding to the nucleic acid of interest, thereby functioning to inhibit expression of the target gene, for example, a sequence capable of inhibiting gene expression of prokaryote.

Further, the target recognition sequence comprising a sequence complementary to a partial sequence of the nucleic acid of interest is effectively delivered to the cell to suppress expression of the nucleic acid of interest, thereby very efficiently inhibiting activity of the target gene. The target recognition sequence is not limited to the completely paired ones, and may comprise non-pairing portions due to mismatch (the corresponding bases are not complementary) or bulge (lacking in the corresponding complementary base on one strand).

Further, the target recognition sequence may comprise modifications obtainable by one or more substitutions, insertions, deletions and combinations thereof, which are functional equivalents having alterations not reducing its activity. For example, the target recognition sequence of the present invention may exhibit 80% or higher, preferably 90%, and more preferably 95% or higher homology to each RNA of the corresponding SEQ ID NO. The homology may be easily determined by comparing the nucleotide sequence with the corresponding region of the target gene using a computer algorithm widely known in the art, for example, Align or BLAST algorithm.

The "target gene" refers to a gene of which expression is inhibited by the target recognition sequence of the present invention, and it may be arbitrarily selected. As the target gene, for example, a gene of which sequence is revealed but functions are not revealed, or a gene of which expression is assumed to cause pathogenesis may be preferably selected.

The "nucleic acid of interest" may be a general bacterial mRNA and the target recognition sequence may be hybridized to a specific region of the nucleic acid of interest, for example, a target region at positions −24 through −5, −19 through +1, and −15 through +5 ('A' of the ATG codon is +1; and the nucleic acids adjacent at the 3'- and 5'-ends relative to the ATG codon are +2 and −1, respectively) near the ribosome binding site of bacterial mRNA, and for example, it may be a nucleic acid molecule targeting a translation initiation region accessible to ribosomes, and also, a sequence which is not the translation initiation region of mRNA (messenger RNA), a functional RNA sequence, etc.

The 'hybridization' means that the target recognition sequence has 80% or higher, for example, 90% or higher, 95% or higher, 98% or higher, 99% or higher, or 100% sequence homology to the base sequence of the region, thereby forming complementary binding.

For example, when the gene of interest is cspE or ompF, the target regions of the nucleic acid of interest, positions −24 to −5, −19 to +1, and −15 to +5 are the same as in the following Table 2.

TABLE 2

| SEQ ID NO | Name | Sequence (5' -> 3') | Position |
|---|---|---|---|
| SEQ ID NO: 5 | cspE mRNA-1 | UAUUUUUCAUGUAAAGGUAA | −24~−5 |
| SEQ ID NO: 6 | cspE mRNA-2 | UUCAUGUAAAGGUAAUUUUG | −19~+1 |
| SEQ ID NO: 7 | cspE mRNA-3 | GUAAAGGUAAUUUUGAUGUC | −15~+5 |
| SEQ ID NO: 8 | ompF mRNA-1 | AAAAAAACCAUGAGGGUAAU | −24~−5 |
| SEQ ID NO: 9 | ompF mRNA-2 | AACCAUGAGGGUAAUAAAUA | −19~+1 |
| SEQ ID NO: 10 | ompF mRNA-3 | UGAGGGUAAUAAAUAAUGAU | −15~+5 |

Further, the target recognition sequences hybridizable to the nucleic acid of interest are the same as in the following Table 3.

TABLE 3

| SEQ ID NO | Name | Sequence (5' -> 3') | Targeting position |
|---|---|---|---|
| SEQ ID NO: 11 | cspE-1 | UUACCUUUACAUGAAAAAUA | −24~−5 |
| SEQ ID NO: 12 | cspE-2 | CAAAAUUACCUUUACAUGAA | −19~+1 |
| SEQ ID NO: 13 | cspE-3 | GACAUCAAAAUUACCUUUAC | −15~+5 |
| SEQ ID NO: 14 | ompF-1 | AUUACCCUCAUGGUUUUUUU | −24~−5 |
| SEQ ID NO: 15 | ompF-2 | UAUUUAUUACCCUCAUGGUU | −19~+1 |
| SEQ ID NO: 16 | ompF-3 | AUCAUUAUUUAUUACCCUCA | −15~+5 |

The target recognition sequence may inhibit gene expression of prokaryote, and the prokaryote may be *E. coli*, *Rhizobium*, *Bifidobacterium*, *Rhodococcus*, *Candida*, *Erwinia*, *Enterobacter*, *Pasteurella*, *Mannheimia*, *Actinobacillus*, *Aggregatibacter*, *Xanthomonas*, *Vibrio*, *Pseudomonas*, *Azotobacter*, *Acinetobacter*, *Ralstonia*, *Agrobacterium*, *Rhizobium*, *Rhodobacter*, *Zymomonas*, *Bacillus*, *Staphylococcus*, *Lactococcus*, *Streptococcus*, *Lactobacillus*, *Clostridium*, *Corynebacterium*, *Streptomyces*, *Bifidobacterium*, *Cyclobacterium*, etc., but it is not limited thereto.

Still another aspect provides a composition for delivering the target recognition sequence, the composition comprising the nucleic acid molecule of the stem-loop structure.

The target recognition sequence may be one or more selected from the group consisting of RNA, RNA aptamer, antisense RNA, and ribozyme, which are hybridizable to a specific region of the nucleic acid of interest (e.g., mRNA), and it may be a sequence consisting of total 10 to 40, 10 to 30, 10 to 20, or 20 nucleotides. Further, the target recognition sequence may complementarily bind to 1 to 40, 10 to 40, 20 to 40, 1 to 20, or 10 to 20 consecutive nucleotide sequences of the nucleic acid of interest. Specifically, the target recognition sequence may form one or more complementary binding to the ribosome binding site (RBS) present in the nucleic acid of interest, and for example, it may form complementary binding to at least one binding nucleotide of the ribosome binding site (RBS) present in the nucleic acid of interest, or complementary binding to 10 to 20 consecutive nucleotide sequences comprising binding nucleotides in the nucleic acid of interest.

The "binding nucleotide" is a nucleotide that exists in the ribosome binding site of the nucleic acid of interest and forms complementary binding to the target recognition sequence.

Still another aspect provides a composition for delivering the target recognition sequence, the composition comprising the nucleic acid complex.

The composition for delivering the target recognition sequence comprise the first nucleic acid molecule comprising the nucleotide sequence of SEQ ID NO: 1 and the second nucleic acid molecule comprising the nucleotide sequence of SEQ ID NO: 4. For example, the first nucleic acid molecule may have the nucleotide sequence of SEQ ID NO: 2 or 3. The first nucleic acid molecule and/or the second nucleic acid molecule may have the stem-loop structure.

Still another aspect provides a method of delivering the target recognition sequence, the method comprising the step of contacting the nucleic acid complex with a cell. The nucleic acid complex is the same as described above.

In the step of contacting the nucleic acid complex with a cell, the cell may be a prokaryotic cell, for example, *E. coli, Rhizobium, Bifidobacterium, Rhodococcus, Candida, Erwinia, Enterobacter, Pasteurella, Mannheimia, Actinobacillus, Aggregatibacter, Xanthomonas, Vibrio, Pseudomonas, Azotobacter, Acinetobacter, Ralstonia, Agrobacterium, Rhizobium, Rhodobacter, Zymomonas, Bacillus, Staphylococcus, Lactococcus, Streptococcus, Lactobacillus, Clostridium, Corynebacterium, Streptomyces, Bifidobacterium, Cyclobacterium*, etc., but it is not limited thereto.

Still another aspect provides a vector comprising DNA encoding the nucleic acid complex.

The vector may comprise a DNA sequence encoding the first nucleic acid molecule comprising the nucleotide sequence of SEQ ID NO: 1, a restriction enzyme site, and a DNA sequence encoding the second nucleic acid molecule comprising the nucleotide sequence of SEQ ID NO: 4.

The first nucleic acid molecule and the second nucleic acid molecule are the same as described above. The DNA sequences encoding these molecules may comprise DNA base sequences complementary to the first nucleic acid molecule and the second nucleic acid molecule. The restriction enzyme site means a site which is recognized and cleaved by a restriction enzyme, and the sequence according to the type of restriction enzyme is known. In the vector, the DNA sequence encoding the first nucleic acid molecule may be linked to the 5'-end of the restriction enzyme site (via a linker or not), and the DNA sequence encoding the second nucleic acid molecule may be linked to the 3'-end of the restriction enzyme site (via a linker or not). The linkage of the DNA sequence may comprise a direct linkage via no linker or a linkage via the above described linker.

When a restriction enzyme recognizing the restriction enzyme site comprised in the vector is treated, the restriction enzyme site is cleaved. A DNA sequence encoding a predetermined nucleic acid sequence (e.g., the target recognition sequence) is inserted into the cleaved site, thereby producing the nucleic acid complex comprising the first nucleic acid molecule, the second nucleic acid molecule, and the nucleic acid of interest sequence (e.g., the target recognition sequence) therebetween.

In an embodiment, the vector may have a base sequence of SEQ ID NO: 21.

Still another aspect provides a vector comprising DNA encoding the nucleic acid complex.

The vector comprising DNA encoding the nucleic acid complex may comprise a DNA sequence encoding the first nucleic acid molecule, a DNA sequence encoding the target recognition sequence, and a DNA sequence encoding the second nucleic acid molecule. In an embodiment, the vector comprising DNA encoding the nucleic acid complex may comprise the DNA sequence encoding the first nucleic acid molecule, the DNA sequence encoding the target recognition sequence, which is linked to the 3' end of the DNA sequence encoding the first nucleic acid molecule, and the DNA sequence encoding the second nucleic acid molecule, which is linked to the 3' end of the DNA sequence encoding the target recognition sequence. The linkage of the DNA sequence may comprise a direct linkage via no linker or a linkage via the above described linker.

In an embodiment, the vector comprising DNA encoding the nucleic acid complex may be obtained by treating the vector comprising the above-described DNA sequence encoding the first nucleic acid molecule, a restriction enzyme site, and the DNA sequence encoding the second nucleic acid molecule with a restriction enzyme, and then cloning the target recognition sequence into the site cleaved by the restriction enzyme.

Still another aspect provides a cell transformed with the vector.

The cell may be a prokaryotic cell, for example, *E. coli, Rhizobium, Bifidobacterium, Rhodococcus, Candida, Erwinia, Enterobacter, Pasteurella, Mannheimia, Actinobacillus, Aggregatibacter, Xanthomonas, Vibrio, Pseudomonas, Azotobacter, Acinetobacter, Ralstonia, Agrobacterium, Rhizobium, Rhodobacter, Zymomonas, Bacillus, Staphylococcus, Lactococcus, Streptococcus, Lactobacillus, Clostridium, Corynebacterium, Streptomyces, Bifidobacterium, Cyclobacterium*, etc., but it is not limited thereto.

Still another aspect provides a method of preparing the nucleic acid complex, the method comprising the step of expressing DNA encoding the nucleic acid complex in the transformed cell.

Unless otherwise defined, all technical and scientific terms used herein have the same meaning as commonly understood by one of ordinary skill in the art to which the invention pertains. Generally, the nomenclature used herein are well known and commonly used in the art.

EXAMPLES

Hereinafter, the present invention will be described in further detail with reference to the following Examples. However, these Examples are illustrative purposes only and are not to be construed to limit the scope of the present invention.

Example 1. Preparation of Target Recognition Sequence

Target recognition sequences recognizing nucleic acids of interest, cspE mRNA and ompF mRNA were prepared, respectively. In detail, target recognition sequences (RNA) complementarily binding to the spanning positions −24 to −5, −19 to +1, −15 to +5 (when +1 is 'A' of the start codon ATG present in the nucleic acid of interest) were designed as in the following Table 4.

TABLE 4

| Nucleic acid of interest | Target site | Name | Sequence (5' -> 3') | SEQ ID NO |
|---|---|---|---|---|
| cspE | −24~−5 region | cspE-1 | UUACCUUUACAUGAAAAAUAS | SEQ ID NO: 11 |
| mRNA | −19~+1 region | cspE-2 | CAAAAUUACCUUUACAUGAAS | SEQ ID NO: 12 |
|  | −15~+5 region | cspE-3 | GACAUCAAAAUUACCUUUACS | SEQ ID NO: 13 |
| ompF | −24~−5 region | ompF-1 | AUUACCCUCAUGGUUUUUUUS | SEQ ID NO: 14 |
|  | −19~+1 region | ompF-2 | UAUUUAUUACCCUCAUGGUUS | SEQ ID NO: 15 |
|  | −15~+5 region | ompF-3 | AUCAUUAUUUAUUACCCUCAS | SEQ ID NO: 16 |

For DNA cloning, double-stranded DNAs were needed, therefore DNAs encoding 6 types of the target recognition sequences (RNA) designed above and sequences complementary thereto were synthesized and prepared (by Bioneer).

Each of the synthesized sequences were dissolved in nuclease-free water at a concentration of 100 pmol/uL, and 1 uL of the solution in which DNA encoding the target recognition sequence was dissolved, and 1 uL of the solution in which the DNA sequence complementary to DNA encoding the target recognition sequence was dissolved were mixed with 48 uL of oligo annealing buffer to prepare total 50 uL of a solution. The temperature of the solution was decreased from 95 C.° to 10° C. at a rate of 5° C. per 5 minutes using a thermal cycler to obtain double-stranded DNA by annealing of the two sequences. Store the annealed products at −20° C.

To phosphorylate 5'-ends, total 50 uL of a reaction solution containing 10 uL (20 pmol) of the double-stranded DNA thus obtained, 1 uL of T4 polynucleotide kinase (Enzynomics), 5 uL of 10× T4 DNA ligase buffer (Enzynomics), and 34 uL nuclease-free water was allowed to react at 37° C. for 30 minutes, and stored at −20° C.

Example 2. Preparation of Recombinant Plasmid 2-1. Preparation of Plasmid DNA pHM-tac plasmid was treated with EcoRI/HindIII restriction enzymes, and cloned with an annealing product of the oligonucleotides given in the following Table 5 to obtain a pHM4T-dSL-SmaI plasmid (Park, H., Bak, G., Kim, S. C. and Lee, Y. (2013) Exploring sRNA-mediated gene silencing mechanisms using artificial small RNAs derived from a natural RNA scaffold in *Escherichia coli*. Nucleic Acids Res. 41, 3787-3804).

The oligonucleotide sequence was a complementary sequence having a cohesive end at its both ends and cloned into a cohesive end produced by treatment of the pHM-tac plasmid with EcoRI/HindIII restriction enzymes.

TABLE 5

| Oligo-nucleotide | Sequence (5' -> 3') | SEQ ID NO |
|---|---|---|
| pHM4T-dSL-SmaI-oligo1 | AATTCGAAGCTGACCAGATCG GTCAGTTTCCCGGGCCCTCGC TTCGGTGAGGGCTTTACCA | SEQ ID NO: 22 |
| pHM4T-dSL-SmaI-oligo2 | AGCTTGGTAAAGCCCTCACCG AAGCGAGGGCCCGGGAAACTG ACCGATCTGGTCAGCTTCG | SEQ ID NO: 23 |

Next, 1 to 2 uL of pHM4T-dSL-SmaI plasmid-containing solution was mixed with 50 uL of chemically competent DH5α *E. coli* cells (Enzynomics, Korea, CP010) and left on ice for 20 minutes, followed by heat shock in a 42° C. water bath for 1 minute. Thereafter, transformation was allowed on ice for 2 minutes.

1 mL of LB medium (1.0 g of NaCl, 0.5 g of yeast extract, and 1.0 g of tryptone dissolved in 100 mL of distilled water, sterilized via autoclaving for 15 min at 121° C.) was added to a reaction solution containing *E. coli* transformed with the pHM4T-dSL-SmaI plasmid, and cultured in a 37° C. shaking incubator for 1 hour.

Next, 1.5 g of micro agar (Duchefa, Nederland, M1002) was added to 1.0 g of NaCl, 0.5 g of yeast extract, and 1.0 g of tryptone, and then they were dissolved in 100 mL of distilled water and sterilized via autoclaving for 15 min at 121° C. 300 uL of the shaking-cultured solution was plated on a LB/Amp agar plate which was supplemented with ampicillin at a concentration of 100 ug/mL, and further cultured in a 37° C. incubator overnight.

Pure colonies were obtained by streaking *E. coli* colonies transformed with the pHM4T-dSL-SmaI plasmid, and then single colony was cultured in 3 mL LB medium containing 100 ug/mL ampicillin in a 37° C. shaking incubator overnight, and finally, a cell transformed with the pHM4T-dSL-SmaI plasmid was obtained.

Figure 1:
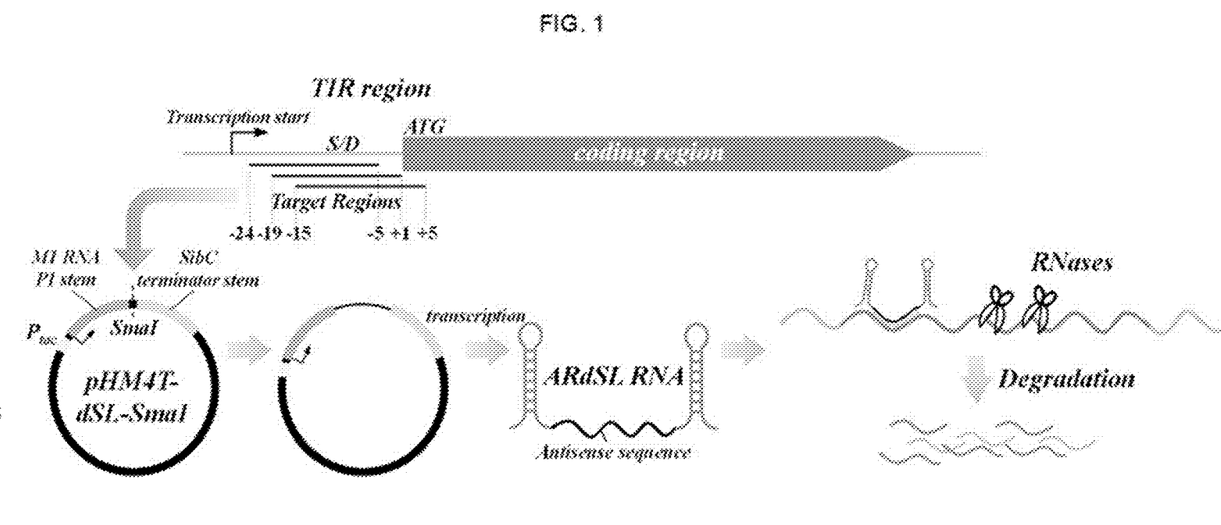
FIG. 1 is a schematic view of gene silencing mediated by interactions between target mRNA and a nucleic acid complex comprising a nucleic acid molecule comprising a stem-loop structure (artificial small regulatory RNAs; afsRNAs) according an embodiment of the present invention.
Figure 2:
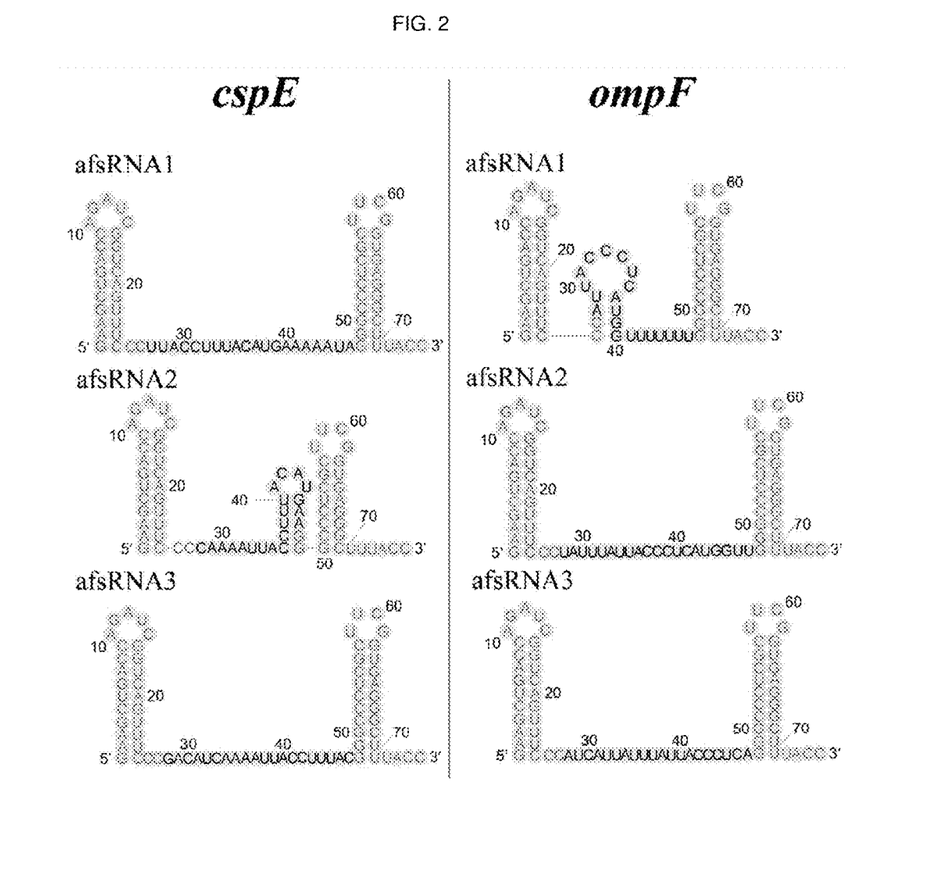
FIG. 2 is a view of the most appropriate secondary structure of the nucleic acid complex according to an embodiment of the present invention, in which the structure predicted using Mfold program has the lowest energy.
Figure 3:
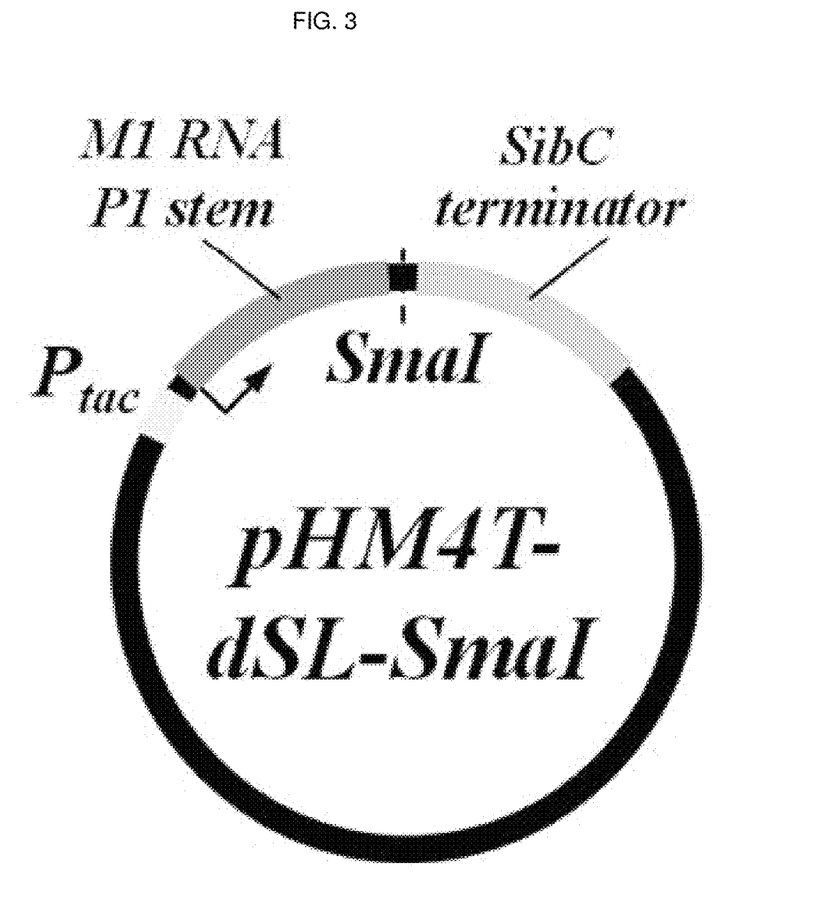
FIG. 3 is a vector map of a pHM4T-dSL-SmaI plasmid used in an embodiment of the present invention.

The pHM4T-dSL-SmaI plasmid (FIG. 3) of SEQ ID NO: 21 was obtained from the cell transformed with the pHM4T-dSL-SmaI plasmid using a plasmid DNA purification kit (Intron Biotechnology, Korea, 17096) according to the manufacturer's protocol, and 3 ug of the obtained plasmid DNA was cleaved using 10× SmaI restriction enzyme (Promega, USA, R6121).

Next, total 100 uL of a reaction solution containing 50 uL (~3 ug) of the cleaved plasmid and 10 uL of 10× restriction enzyme buffer (Promega, USA, R6121), 37 uL of Nuclease-free water, and 3 uL of SmaI restriction enzyme (Promega, USA, R6121) was prepared and allowed to react at 25° C. for 4 to 6 hrs, and transferred at 65° C., and then allowed to react for 20 minutes to inactivate the restriction enzyme.

Next, for dephosphorylation to prevent the plasmid linearized by the restriction enzyme from rebinding, 10 uL of 10× Antarctic phosphatase reaction buffer (New England BioLabs, England) was added to the restriction enzyme-inactivated reaction solution, and 1 uL of Antarctic phosphatase (New England BioLabs, England, M0289) was added thereto and mixed well, and allowed to react in a 37° C. water bath for 25 minutes, followed by heating at 65° C. for 10 minutes for deactivation of phosphatase.

Next, the phosphatase-inactivated reaction solution was electrophoresed on a 1% agarose gel, and a linearized and dephosphorylated DNA band of 4268 bp was excised from the gel.

Thereafter, DNA was purified using a spin column-based gel extraction kit (Intron Biotechnology, Korea, 17288) and purity and amount of DNA were measured using a Nanodrop (ThermoScientific, USA). As a result, the purity was about 2.0 as OD260/OD280 value and concentration of the dephosphorylated linear plasmid DNA was 10 ng/uL or higher.

2-2. DNA Ligation and Transformation

The double-stranded DNA prepared in Example 1 and the plasmid DNA prepared in Example 2-1 were mixed at a molar ratio of 1:3 to 1:6 to a final concentration of 4 uL or less. Next, 5 uL of 2× rapid ligation buffer (Promega, USA, C6711; 60 mM Tris-HCl (pH 7.8), 20 mM $MgCl_2$, 20 mM DTT, 2 mM ATP and 10% PEG) and 1 uL of T4 ligase (Enzynomics, Korea, M019) were added and then nuclease-free water was added up to 10 uL, and allowed to react at 4° C. for 4 hours or longer to ligate the double stranded DNA with the plasmid.

1 to 2 uL of a reaction solution containing the double stranded DNA-ligated plasmid was mixed with 50 uL of chemically competent DH5α E. coli cells (Enzynomics, Korea, CP010), and left on ice for 20 minutes. Then, the solution was subjected to heat shock in a 42° C. water bath for 1 minute and left on ice for 2 minutes for transformation.

2-3. Production of Recombinant Plasmid 1 mL of LB medium (1.0 g of NaCl, 0.5 g of yeast extract, and 1.0 g of tryptone dissolved in 100 mL of distilled water, sterilized via autoclaving for 15 min at 121° C.) was added to the reaction solution containing E. coli transformed in Example 2-2, and cultured in a 37° C. shaking incubator for about 1 hour.

Next, 1.5 g of micro agar (Duchefa, Nederland, M1002) was added to 1.0 g of NaCl, 0.5 g of yeast extract, and 1.0 g of tryptone, and then they were dissolved in 100 mL of distilled water and sterilized via autoclaving for 15 min at 121° C. 300 uL of the shaking-cultured solution was plated on a LB/Amp agar plate which was supplemented with ampicillin at a concentration of 100 ug/mL, and further cultured in a 37° C. incubator overnight.

Pure colonies were obtained by streaking the transformed E. coli colonies, and then single colony was cultured in 3 mL LB medium containing 100 ug/mL ampicillin in a 37° C. shaking incubator overnight, and finally, a transformed cell was obtained.

The recombinant plasmid DNA was obtained from the transformed cell using a plasmid DNA purification kit (Intron Biotechnology, Korea, 17096), and the recombinant plasmid DNA was identified by DNA sequencing analysis (Sanger method), and concentration and purity of the identified recombinant plasmid DNA were measured using a NanoDrop 1000 (ThermoScientific, USA), and stored at −20° C.

As a result of measuring the concentration and purity of the plasmid DNA, the concentration was 50 ng/uL or higher, and purity was about 2.0 as OD260/OD280 value.

Example 3. Evaluation of Gene Silencing Effect

In order to examine whether afsRNA expressed by the recombinant plasmid of Example 2 can be used as a routine method for silencing of gene of interest, two mRNA targets (cspE mRNA and ompF mRNA) were selected in E. coli MG1665 and used for test, and these two mRNAs are expressed as monocistronic mRNA. In general, all samples containing RNA were incubated on ice, unless otherwise specified. RNase-free conditions were maintained for RNA work 3-1. Preparation of E. coli E. coli MG1655 (Coli Genetic Stock Center (CGSC), CGSC #7740) was cultured in a shacking incubator under conditions of 200 rpm and 37° C. for 16 hours, and 30 uL of the obtained E. coli was added to in fresh 3 mL LB/Amp medium (1.0 g of NaCl, 0.5 g of yeast extract, and 1.0 g of tryptone were dissolved in 100 mL of distilled water, sterilized via autoclaving for 15 min at 121° C., and ampicillin was added at a final concentration of 100 ug/mL) (1:100 dilution), and cultured in a 37° C. shaking incubator until $OD_{600}$ reached about 0.5. Then, E. coli was harvested by centrifugation at 4° C., 5,000 g for 2 minutes.

Next, ice-cold 0.01 M NaCl (500 uL) was added to the harvested cells and resuspended via pipetting until all pellets disappeared, followed by centrifugation at 4° C., 5,000 g for 2 minutes to precipitate the bacterial cells and to discard the supernatant.

Next, ice-cold 0.03 M $CaCl_2$ (500 uL) was added and resuspended, and left on ice for 20 minutes, followed by centrifugation at 4° C., 5,000 g for 2 minutes to precipitate the bacterial cells and to discard the supernatant. Ice-cold 0.03 M $CaCl_2$ (100 uL) was added to the pellet and resuspended via pipetting. Next, 10 to 100 ng of the recombinant plasmid DNA was added thereto, and left on ice for 10 minutes, and then heat-shocked at 42° C. for 1 minute, and then left on ice for 2 minutes.

1 mL of LB medium (1.0 g of NaCl, 0.5 g of yeast extract, and 1.0 g of tryptone dissolved in 100 mL of distilled water, sterilized via autoclaving for 15 min at 121° C.) was put in each tube, and 300 uL thereof was plated on an LB/Amp agar plate (1.5 g of micro agar (Duchefa, Nederland, M1002) was added to 1.0 g of NaCl, 0.5 g of yeast extract, and 1.0 g of tryptone, and they were dissolved in 100 mL of distilled water, and sterilized via autoclaving for 15 min at 121° C. and ampicillin was added at a final concentration of 100 ug/mL), and the plate was turned upside down and incubated at 37° C. overnight. A single colony was cultured by streaking the transformed colonies so as to prepare freezer stocks.

Further, a control E. coli was obtained in the same manner as above, except that pHM4T-dSL-SmaI plasmid without the target recognition sequence was used as an empty vector, instead of the recombinant plasmid.

3-2. Preparation of Total RNA

The transformed E. coli colonies obtained in Example 4-1 were incubated in 3 mL LB/Amp medium in a shaking incubator under conditions of 200 rpm and 37° C. for 16 hours. Next, the culture was diluted (1/100), and cultured in a fresh LB/Amp medium for 3 to 4 hours until $OD_{600}$ reached about 1.0. IPTG was added to a final concentration of 1 mM and the cells were further cultured for 20 minutes to induce afsRNA expression.

Next, afsRNA expressed in the cells was stabilized by addition of two volumes of RNA protect Bacteria Reagent, and stirred for 5 seconds, and left for 5 minutes at room temperature. Next, centrifugation was performed at 5,000 g for 10 minutes and the supernatant was discarded to obtain E. coli.

200 uL (1 mg/mL) of lysozyme solution was added for disruption of the cell wall of the obtained E. coli, and allowed to react for 10 minutes while vortexing at room temperature. Total RNA was purified from the cell wall-disrupted E. coli using an RNeasy mini kit.

In detail, a spin column-based RNA purification kit (QIAGEN, 74104) was used according to the manufacturer's specifications to bind RNA to the spin column. After a washing process, RNA bound to the spin column was dissolved in 50 uL of nuclease-free water to purify RNA. The purified RNA was stored at −70° C. Its final concentration was >500 ng/uL.

Further, purified RNA of the control *E. coli* was obtained in the same manner as above, except that the control *E. coli* colony of Example 4-1 was used.

3-3. DNase Treatment

To remove contaminated genomic DNA, a Turbo DNA-Free™ DNase Kit reaction solution was mixed as in the following Table 6 and prepared in a PCR tube. A solution containing the purified RNA obtained in Example 3-2 was added to the prepared PCR tube, and allowed to react at 37° C. for 30 minutes. Additionally, 2 U of DNase I was added again and allowed to react at 37° C. for 30 minutes. 10 uL (0.2 volumes) of inactivation slurry containing the inactivation reagent of DNase I was added. Since the slurry tends to sink, vortexing was performed well before adding. The reaction solution was reacted at room temperature for 10 minutes while vortexing the solution for 5 seconds every 2 minutes. The solution was precipitated by centrifugation at 10,000 g for 1.5 minutes to collect 50 uL of the supernatant, which was stored at −70° C.

The purified RNA of the control *E. coli* of Example 3-2 was also treated in the same manner as above to remove contaminated DNA.

TABLE 6

| | |
|---|---|
| Purified total RNA + Nuclease-free water | 10 ug in 50 uL |
| 10x Turbo DNase buffer | 5 uL |
| Turbo DNase I (2U/uL) | 1 uL (2U) |
| Total | 66 uL |

3-4. cDNA Synthesis

For synthesis of cDNA strand for the total RNA of Example 3-2, a reaction solution was prepared as in the following Table 7, and mixed well by vortexing. The reaction solution was reacted at 50° C. for 60 minutes and heated at 95° C. for 5 minutes using a PCR machine (C1000, BioRad, USA) to inactivate reverse transcriptase. The cDNA was stored at −20° C. until the real-time PCR reaction.

TABLE 7

| | |
|---|---|
| DNase-treated total RNA | 4 uL (~800 ng) |
| Nuclease-free water | 14 uL |
| Random hexamer (dN6) | 2 uL (50 pmol) |
| TOPscript ™ RT DryMIX | 1 tube |
| Total | 20 uL |

3-5. qPCR Analysis of Gene Expression Suppression

For qPCR analysis of each target gene, primers of the following Table 8 were prepared. The primers should have the least self complementarity to avoid dimers, and the PCR product should be generally about 100 bp.

TABLE 8

| Primer | Sequence (5' -> 3') | SEQ ID NO: |
|---|---|---|
| cspE_F | GTCCAAAGGATTCGGTTTCA | SEQ ID NO: 17 |
| cspE_R | CAGAGCGATTACGTTTGCAG | SEQ ID NO: 18 |
| ompF_F | AGGCTTTGGTATCGTTGGTG | SEQ ID NO: 19 |
| ompF_R | TGCGCAACTAACAGAACGTC | SEQ ID NO: 20 |

In detail, 1 uL of DNase I (2 U/uL) was added to 1 mL of qPCR premix, and allowed to react at 37° C. for 30 minutes to remove contaminated genomic DNA. 1 uL of DNase I was further added, and allowed to react at 37° C. for 30 minutes, and heated at 75° C. for 15 minutes to inactivate DNase I. Then, the solution was left on ice. Next, total 50 uL of a quantitative Real-Time PCR solution containing each 1 uL (10 pmol) of Gene-specific primer, 2 uL of template cDNA, 25 uL of TOPreal™ qPCR 2× PreMIX, and 21 uL of Nuclease-free water was prepared.

The reaction solution was put in a qPCR tube and then mixed well by vortexing, followed by spinning down. The tube was placed in a Real-time PCR machine (Exicycler™ 96, Bioneer, Korea), and PCR was performed as in the following Table 9 to amplify the gene.

TABLE 9

| | Temperature | Time | Note |
|---|---|---|---|
| 1 cycle | 95° C. | 10 min | |
| 40 cycles | 95° C. | 30 s | |
| | 57-60° C. | 30 s | |
| | 72° C. | 20 s | (depending on the product size) |
| 1 cycle | 25° C. | 10 min | (or melting step at 65-95° C.) |

Figure 4:
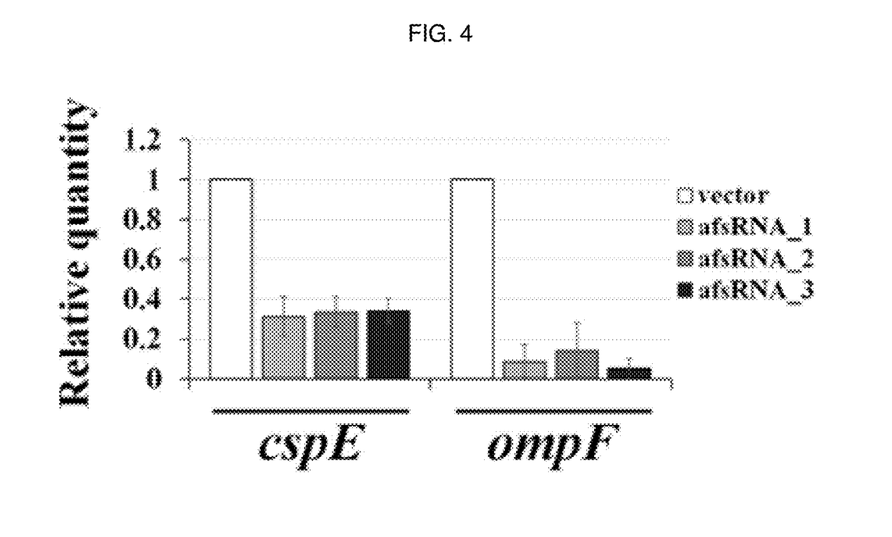
FIG. 4 is a graph showing a comparison between cspE mRNA (left) and ompF mRNA (right) expression levels relative to an empty vector as a control group after treatment of the nucleic acid complex of an embodiment of the present invention.

Following the PCR reaction, agarose gel electrophoresis was performed to examine specific gene amplification. The result was analyzed by the $ddC_T$ method (Kenneth J. Livak and Thomas D. Schmittgen. Analysis of Relative Gene Expression Data Using Real-Time Quantitative PCR and the 2-[Delta][Delta]$C_T$ Method. Methods, 25(4):402-408, 2001), and the relative quantity of mRNA was compared. The result is shown in FIG. 4.

Further, for control test, 4 samples were prepared as follows to perform PCR in the same manner as in the above Example.

Control Group 1) pHM4T-dSL-SmaI Plasmid Sample for Comparing Quantity of Target mRNAs.

TABLE 10

| | |
|---|---|
| Gene-specific primers | 1 uL each |
| | (10 pmol) |
| Template cDNA(control group of pHM4T-dSL-SmaI) | 2 uL |
| TOPreal ™ qPCR 2x PreMIX | 25 uL |
| Nuclease-free water | 21 uL |
| Total | 50 uL |

Control group 1) is a control group using cDNA of RNA which was extracted from the strain having only pHM4T-dSL-SmaI empty plasmid in order to monitor whether mRNA quantity is changed by expression of afsRNA. The result is shown in FIG. 4. In FIG. 4, the column indicated by vector represents the result of Control group 1).

As shown in FIG. 4, quantity of the target mRNA was greatly reduced in strains expressing individual afsRNAs, compared to the control group. The expression quantity of cspE mRNA was reduced up to 30%, and the expression quantity of ompF mRNA was reduced up to 10%.

Control Group 2) 16S rRNA (rrsA) for Cell Normalization

TABLE 11

| rrsA sense primer | 1 uL (10 pmol) |
|---|---|
| rrsA antisense primer | 1 uL (10 pmol) |
| Template cDNA | 2 uL |
| TOPreal ™ qPCR 2x PreMIX | 25 uL |
| Nuclease-free water | 21 uL |
| Total | 50 uL |

Control group 2) is a control group using 16S rRNA which shows little change in all samples, in order to use the ddC$_T$ method.

Control Group 3) No Reverse Transcription Control Group:

TABLE 12

| Gene-specific primers or rrsA primers | 1 uL each (10 pmol) |
|---|---|
| DNase-treated RNA mixture of pHM4T-dSL-SmaI control or target afsRNAs | 2 uL |
| TOPreal ™ qPCR 2x PreMIX | 25 uL |
| Nuclease-free water | 21 uL |
| Total | 50 uL |

Control group 3) is a control group to monitor whether the qPCR result was obtained from the DNA-contaminated RNA sample by performing qPCR of a sample containing no reverse transcriptase in the same manner.

Control Group 4) No Template Control Group:

TABLE 13

| Gene-specific primers or rrsA primers | 1 uL each (10 pmol) |
|---|---|
| TOPreal ™ qPCR 2x PreMIX | 25 uL |
| Nuclease-free water | 23 uL |
| Total | 50 uL |

Control group 4) is a control group to monitor whether other solutions (TOPreal qPCR premix, water, primers, etc.) used in qPCR were contaminated with DNA by performing qPCR without the template.

What is claimed is:

1. A nucleic acid complex, comprising:
a first nucleic acid molecule, a target recognition sequence, and a second nucleic acid molecule arranged in 5' to 3' direction of the nucleic acid complex,
wherein the first nucleic acid molecule comprises a nucleotide sequence of SEQ ID NO: 2 or SEQ ID NO: 3, and
the second nucleic acid molecule comprises a nucleotide sequence of SEQ ID NO: 4, and
the target recognition sequence is 10 to 40 nucleotides in length and complementarily binds to 10 to 40 consecutive nucleotides of a nucleic acid of interest.

2. The nucleic acid complex of claim 1, further comprising a nucleic acid linker consisting of 1 to 20 nucleotides in length, which is linked to the 3'-end of the first nucleic acid molecule and the 5'-end of the target recognition sequence.

3. The nucleic acid complex of claim 1, wherein the target recognition sequence is one or more selected from the group consisting of RNA, RNA aptamer, antisense RNA, and ribozyme.

4. The nucleic acid complex of claim 3, wherein the target recognition sequence complementarily binds to 10 to 20 consecutive nucleotides of the nucleic acid of interest, wherein the 10 to 20 consecutive nucleotide sequences includes at least one binding nucleotide of a ribosome-binding site (RBS).

5. The nucleic acid complex of claim 4, wherein the ribosome binding site is at positions −24 to −5, −19 to +1, or −15 to +5 when +1 is 'A' of the start codon ATG present in the nucleic acid of interest.

6. The nucleic acid complex of claim 4, wherein the nucleic acid of interest is a sequence which is not the translation initiation region of mRNA (messenger RNA) or a functional RNA sequence.

7. The nucleic acid complex of claim 4, wherein the nucleic acid of interest consists of a nucleotide sequence selected from the group consisting of SEQ ID NOS. 5 to 10.

8. The nucleic acid complex of claim 1, wherein the target recognition sequence consists of a nucleotide sequence selected from the group consisting of SEQ ID NOS. 11 to 16.

9. The nucleic acid complex of claim 1, wherein the target recognition sequence suppresses gene expression of a prokaryote.

10. The nucleic acid complex of claim 9, wherein the prokaryote is selected from the group consisting of *E. coli, Rhizobium, Bifidobacterium, Rhodococcus, Candida, Erwinia, Enterobacter, Pasteurella, Mannheimia, Actinobacillus, Aggregatibacter, Xanthomonas, Vibrio, Pseudomonas, Azotobacter, Acinetobacter, Ralstonia, Agrobacterium, Rhizobium, Rhodobacter, Zymomonas, Bacillus, Staphylococcus, Lactococcus, Streptococcus, Lactobacillus, Clostridium, Corynebacterium, Streptomyces, Bifidobacterium*, and *Cyclobacterium*.

11. A vector comprising DNA encoding the nucleic acid complex of claim 1.

12. The vector of claim 11, wherein the vector comprises a DNA sequence encoding a first nucleic acid molecule consisting of the nucleotide sequence of SEQ ID NO: 1, a restriction enzyme site, and a DNA sequence encoding a second nucleic acid molecule consisting of a nucleotide sequence of SEQ ID NO: 4.

13. The vector of claim 12, wherein the vector consists of the nucleotide sequence of SEQ ID NO: 21.

14. A cell transformed with the vector of claim 11.

15. The cell of claim 14, wherein the cell is a prokaryotic cell.

\* \* \* \* \*